(12) United States Patent
Pronk (10) Patent No.: US 9,901,578 B2
(45) Date of Patent: Feb. 27, 2018

(54) COMBINATION OF 10-PROPARGYL-10-DEAZAAMINOPTERIN AND ERLOTINIB FOR THE TREATMENT OF NON-SMALL CELL LUNG CANCER

(71) Applicant: Allos Therapeutics, Inc., Westminster, CO (US)

(72) Inventor: Gijsbertus J. Pronk, Westminster, CO (US)

(73) Assignee: ALLOS THERAPEUTICS, INC., Westminster, CO (US)

( * ) Notice: Subject to any disclaimer, the term of this patent is extended or adjusted under 35 U.S.C. 154(b) by 255 days.

(21) Appl. No.: 13/944,596

(22) Filed: Jul. 17, 2013

(65) Prior Publication Data

US 2013/0303536 A1  Nov. 14, 2013

Related U.S. Application Data

(63) Continuation-in-part of application No. 12/779,852, filed on May 13, 2010, now abandoned, which is a continuation-in-part of application No. 12/193,518, filed on Aug. 18, 2008, now abandoned.

(60) Provisional application No. 60/956,525, filed on Aug. 17, 2007, provisional application No. 61/044,823, filed on Apr. 14, 2008.

(51) Int. Cl.
*A61K 31/519* (2006.01)
*A61K 31/517* (2006.01)
*A61K 31/5377* (2006.01)

(52) U.S. Cl.
CPC .......... *A61K 31/519* (2013.01); *A61K 31/517* (2013.01); *A61K 31/5377* (2013.01); *G01N 2333/485* (2013.01); *G01N 2800/52* (2013.01)

(58) Field of Classification Search
CPC ............... A61K 31/519; A61K 31/517; A61K 31/5377; G01N 2333/485; G01N 2800/52
See application file for complete search history.

(56) References Cited

U.S. PATENT DOCUMENTS

| | | | |
|---|---|---|---|
| 4,393,064 A | 7/1983 | Degraw, Jr. et al. | |
| 4,433,147 A | 2/1984 | Degraw, Jr. et al. | |
| 4,652,533 A | 3/1987 | Jolley | |
| 4,843,155 A | 6/1989 | Chomczynski | |
| 5,066,828 A | 11/1991 | Bey et al. | |
| 5,286,726 A | 2/1994 | Bey et al. | |
| 5,354,751 A | 10/1994 | DeGraw, Jr. et al. | |
| 5,374,726 A | 12/1994 | DeGraw | |
| 5,981,592 A | 11/1999 | Wechter et al. | |
| 6,028,071 A | 2/2000 | Sirotnak et al. | |
| 6,100,411 A | 8/2000 | Ojima | |
| 6,323,205 B1 | 11/2001 | Sirotnak et al. | |
| 6,410,696 B1 | 6/2002 | Davalian et al. | |
| 7,622,470 B2 | 11/2009 | O'Connor et al. | |
| 7,939,530 B2 | 5/2011 | O'Connor et al. | |
| 8,299,078 B2 | 10/2012 | O'Connor et al. | |
| 8,835,433 B2 | 9/2014 | Pronk | |
| 2004/0028607 A1 | 2/2004 | Verdin et al. | |
| 2005/0148029 A1 | 7/2005 | Buechler et al. | |
| 2005/0267117 A1 | 12/2005 | O'connor et al. | |
| 2006/0121085 A1 | 6/2006 | Warren et al. | |
| 2007/0093969 A1 | 4/2007 | Mendrick et al. | |
| 2008/0058280 A1 | 3/2008 | O'Connor et al. | |
| 2008/0108091 A1 | 5/2008 | Hennessy et al. | |
| 2011/0190305 A1 | 8/2011 | Pronk | |
| 2013/0143891 A1 | 6/2013 | Pronk | |
| 2013/0178441 A1 | 7/2013 | Fruchtman | |
| 2013/0197004 A1 | 8/2013 | Pronk | |
| 2014/0364437 A1 | 12/2014 | Pronk | |

FOREIGN PATENT DOCUMENTS

| | | |
|---|---|---|
| JP | 07506369 | 7/1995 |
| JP | 07506369 A | 7/1995 |
| JP | 2001-505537 | 4/2001 |
| JP | 2001505537 A | 4/2001 |
| JP | 2008501038 A | 1/2008 |
| WO | WO 98/02163 | 1/1998 |
| WO | WO 03/045429 | 12/2003 |
| WO | WO 05/117891 | 12/2005 |
| WO | WO 05/117892 | 12/2005 |
| WO | WO 2011/096947 | 8/2011 |
| WO | WO 2011/153368 | 12/2011 |
| WO | WO 2012/021392 | 2/2012 |

OTHER PUBLICATIONS

National Comprehensive Cancer Network, www.nccn.org "Non-Hodgkins's Lymphomas" V.3.2008, Apr. 10, 2008.
Starling et al. (1974) Cancer Chemotherapy Reports 58:683-687 "Drug trials in neuroblastoma: cyclophosphamide (NSC-26271) Alone; Vincristine (NSC-67574) plus cyclophosphamide; 6-mercaptopurine (NSC-755) plus 6-methylmercaptopurine riboside (NSC-40774); and Dcy10sine arabinoside (NSC-63878) alone".
European Search Report for Application No. EP11790419 dated Jun. 18, 2013.
Sausville et al. Cancer Research, 2006, vol. 66 pp. 3351-3354.
Johnson et al. British J. of Cancer, 2001, 84(10): 1424-1431.
Canadian Search report for Application No. 2788554 dated Mar. 3, 2015.
Food and Drug Administration (Sep. 24, 2009) "NDA #022468" documents—Part 1.
Food and Drug Administration (Sep. 24, 2009) "NDA #022468" documents—Part 2.
Giaccone et al. (1996) The Oncologist 1:82-87, "Drug Resistance".
Giovanetti et al., "Synergistic Cytotoxicity and Pharmacogenetics of Gemcitabine and Pemetrexed Combination in Pancreatic Cancer Cell Lines" Clinical Cancer Research (2004) vol. 10 pp. 2936-2943.

(Continued)

*Primary Examiner* — Kara R McMillian
(74) *Attorney, Agent, or Firm* — Swanson & Bratschun, L.L.C.

(57) ABSTRACT

The present invention relates to compositions comprising a combination of 10-propargyl-10-deazaaminopterin and an EGFR Kinase inhibitor, including erlotinib, for treatment of non-small cell lung cancer, and methods of treatment for non-small cell lung cancer in a patient in need thereof comprising administering for combination of 10-propargyl-10-deazaaminopterin and an EGFR Kinase inhibitor, including erlotinib, for treatment of non-small cell lung cancer.

3 Claims, 5 Drawing Sheets

(56) References Cited

OTHER PUBLICATIONS

Janeway-Travers. "Immunobiology: the immune system in health and disease" 1996, 2nd edition.
Teicher et al., "Treatment Regimens Including the Multitargeted Antifolate LY231514 in Human tumor Xenografts"Cinical Cancer Researh (2000) vol. 6 pp. 1016-1023.
Tonkinson et al., "Cell Cycle Modulation by a Multitargeted Antifolate, LY231514, Increases the Cytotoxicity and Antitumor Activity of Gemcitabine in HT29 Colon Carcinoma" Cancer.
Chinese Search Report in English only for Application No. 2011800385386 dated Dec. 19, 2013.
European Search Report for Application No. 11816854.1 dated Jul. 23, 2013.
Allos Therapeutics, Inc. (May 15, 2008) Drugs.com: Press Release "Allos Therapeutics Reports Interim Response and Safety Data from Pivotal Phase 2 PROPEL Trial".
Coiffier et al. (Jun. 15-18, 2011) International Conference of Myeloma and Lymphoma, Lugano, Switzerland, Poster: "Pralatrexate Reverses the Trend to Progressive Resistance in Patients With Relapsed/Refractory Peripheral T-Cell Lymphoma (PTCL)".
Courtenay et al. (1980) Nature 283:666-668 "Immunisation against heterologous type II collagen induces arthritis in mice".
DeGraw et al. (1986) Journal of Medicinal Chemistry 29(6):1056-1061 "Synthesis and biological activity of resolved carbon-10 diastereomers of 10-methyl- and 10-ethyl-10-deazaminopterin".
Dörwald (2005) Side Reactions in Organic Synthesis: A Guide to Successful Synthesis Design, Weinheim: Wiley-VCH Verlag GmbH & Co. KGaA, Preface.
Folotyn (pralatrexate injection) (Sep. 24, 2009) Package Insert: "Highlights of Prescribing Information" 16 pages.
Goy et al. (Dec. 10-13, 2011) $53^{rd}$ ASH Annual Meeting and Exposition, San Diego, California, Paper: "Pralatrexate Is Effective in Patients with Relapsed or Refractory Peripheral T-Cell Lymphoma (PTCL) with Prior Ifosfamide, Carboplatin, and Etoposide (ICE)—Based Regimens".
Grant et al., "Phase II Trials in Small-Cell Lung Cancer: Shouldn't We Be Doing Better?", Journal of the National Cancer Institute, (1992) vol. 84, 1058-1059.
Highlights of Prescribing Information at http://www.accessdata.fda.gov/drugsatfdadocs/label/2009/0224681.pdf.
Hum et al., (1996) "Folate, antifolates, and folate analogs in Pediatric Oncology", Invest. New Drugs 14:101-111.
International Search Report and Written Opinion for PCT/US10/26262, dated Apr. 23, 2010, 19 pages.
International Search Report and Written Opinion for PCT/US11/38953, dated Sep. 12, 2011, 34 pages.
International Search Report and Written Opinion for PCT/US11/46711, dated Dec. 20, 2011, 6 pages.
Jordan (2003) Nature Reviews 2:205-213 "Tamoxifen: A Most Unlikely Pioneering Medicine".
Kamen (1997) "Folate and Anti-folate Pharmacology" Sem. in Oncol. 24(5):S18-30 to S18-39.
Malik et al. (2010) Clin Cancer Res. 16(20):4921-4927 "Folotyn (pralatrexate injection) for the treatment of patients with relapsed or refractory peripheral T-cell lymphoma: U.S. Food and Drug Administration drug approval summay".
Mangone et al. (Dec. 10-13, 2011) 53rd ASH Annual Meeting and Exposition, San Diego, California, Abstract: "Pralatrexate Has Potent Activity Against Multiple Myeloma In Vitro and In Vivo, and Activity Correlates with Tumor RFC-1 and DHFR Expression".
McGuire, "Anticancer Antifolates: Current Status and Future Directions", (2003) in Current Pharmaceutical Design, 9(31) pp. 2593-2613.
Montgomery et al., (1979) "Analogues of Methotrexate", J. Med. Chem., 22(7):862-868.
Mould et al. (2009) Clinical Pharmacology & Therapeutics 86(2):190-196 "A Population Pharmacokinetic and Pharmacodynamic Evaluatioin of Pralatrexate in Patients With Relapsed or Refractory Non-Hodgkin's or Hodgkin's Lymphoma".

O'Connor et al. (2011) Journal of Clinical Oncology 29(9):1182-1189 "Pralatrexate in patients with relapsed or refractory peripheral T-Cell lymphoma (PTCL): results from the pivotal PROPEL study".
Rueda et al. (2009) Clin Transl Oncol 11:215-220 "Pralatrexate, a new hope for aggressive T-cell lymphomas?".
Serajuddin (2007) Advanced Drug Delivery Reviews 59:603-616 "Salt formation to improve drug solubility".
Shustov et al. (2010) Journal of Clinical Oncology, ASCO Annual Meeting Proceedings 28(15):Abstract No. 8054 "Pralatrexate in patients with relapsed/refractory peripheral T-cell lymphoma (PTCL): Relationship between response and survival".
Shustov et al. (Aug. 15-19, 2011) Pan Pacific Lymphoma Conference, Koloa, Hawaii, Poster: "Pralatrexate: An Effective Single-Agent, Second-Line Treatment in Patients With Relapsed/Refractory Peripheral T-Cell Lymphoma (PTCL) Following Failure of Cyclophosphamide/Doxorubicin/Vincristine/Prednisone (CHOP)".
Shustov et al. (Aug. 15-19, 2011) Pan Pacific Lymphoma Conference, Koloa, Hawaii, Presentation Outline: "Pralatrexate: An Effective Single-Agent, Second-Line Treatment in Patients With Relapsed/Refractory Peripheral T-Cell Lymphoma (PTCL) Following Failure of Cyclophosphamide/Doxorubicin/Vincristine/Prednisone (CHOP)".
Akutsu et al., (2002) "Schedule-dependent Synergism and Antagonism Between Methotrexate and Cytarabine Against Human Leukemia Cell Lines in Vitro" Leukemia 16:1808-1817.
Allos Therapeutics, Inc., "Allos Therapeutics Reports Interim Response and Safety Data from Pivotal Phase 2 Propel Trial" May 15, 2008 (Press Release).
Allos Therapeutics, Inc., "Results Reproted at the American Society of Hematology Annual Meeting Affirm Impressive Activity of Allos Therapeutics' Novel Antifolate PDX in Patients with Peripheral T-Cell Lymphoma." Dec. 11, 2006 (Press Relase).
Arango et al. (2009) Clinical Lung Cancer 10(2):91-98 "Second-Line Therapy for Non-Small-Cell Lung Cancer".
Assaraf, Yehuda G. (2007) "Molecular Basis of Antifolate Resistance" Cancer Metastasis Rev. 26:153-181 Springer.
Au et al. (2000) "Aggressive subcutaneous panniculitis-like T-cell lymphoma: complete remission with fludarabine, mitoxantrone and dexamethasone" British Journal of Dermatology, 143:408-410.
Ausubel, et al., "Current Protocols in Molecular Biology" 1987, Current Protocols, vol. 2.
Awar et al., (2007) "Treatment of Transformed Mycosis Fungoides with Intermittent Low-Dose Gemcitabine" Oncology 73:103-135, Department of Internal Medicine.
Azzoli et al., (2007) "A Phase 1 Study of Pralatrexate in Combination with Paclitaxel or Docetaxel in Patients with Advance Solid Tumors" Clin. Cancer Res. 13(9):2692-2698.
Barberio et al., (2007) "Transformed Mycosis Fungoides: Clinicopathological Features and Outcome" British Journal of Dermatology 157:284-289, British Association of Dermatologists.
Barredo et al., (1994) "Differences in Constitutive and Post-Methotrexate Folylpolyglutamate Synthetase Activity in B-Lineage and T-Lineage Leukemia" Blood 84(2)564-569.
Bekkenk et al., (2003) "Peripheral T-Cell Lymphomas Unspecified Presenting in the Skin: Analysis of Prognostic Factors in a Group 82 Patients" Blood 102(6):2213-2219, The American Society of Hematology.
Burg et al., (2005) "WHO/EORTC Classification of Cutaneous Lymphomas 2005: Histological and Molecular Aspects" Journal of Cutaneous Pathology 32:647-674, Blackwell Munksgaard.
Burg et al., (2007) "Cutaneous Lymphomas Current and Future Concepts" J. Egypt Wom. Dermatol. Soc. 4(1):1-23.
Cadman and Eiferman (1979) "Mechanism of Synergistic Cell Killing When Methotrexate Precedes Cytosine Arabinoside" J. Clin. Invest. 64:788-797.
Chau et al., (2002) "Gemcitabine and It's Combinations in the Treatment of Malignant Lymphoma" Clinical Lymphoma 3:97-104.
Cheson et al., (1999) "Report of an International Workshop to Standardize Response Criteria for Non-Hodgkin's Lymphoma's" 17(4):1244-1253, Journal of Clinical Oncology.
Connors et al., (2002) "Lymphoma of the Skin" Hematology 263-282, American Society of Hematology.

(56) References Cited

OTHER PUBLICATIONS

DeGraw et al., (1982) "Synthesis and Antitumor Activity of 10-Alkyl-10-deazaminopterins. A convenient Synthesis of 10-Deazaaminopterin." J. Med. Chem. 25:1227-1230, American Chemical Society.

Degraw et al., (1993) "Synthesis and Antitumor Activity of 10-propargyl-10-deazaaminopterin" Journal of Medicinal Chemistry, 36:2228-2231.

Degraw et al., (1995) "New Analogs of Methotrexate in Cancer and Arthritis." Current Medicinal Chemistry, 2:630-653.

Diamandidou et al., (1998) "Transformation of Mycosis Fungoides/Sezary Syndrome: Clinical Characteristics and Prognosis" Blood 92:1150-1159.

Diddens et al., (1983) patterns of Cross-Resistance to the Antifolate Drugs Trimetrexate, Metoprine, Homofolate, and CB3717 in Human Lymphoma and Osteosarcoma Cells Resistant to Methotrexate Cancer Research 43:5286-5292.

Dmitrovsky et al., (1987) "Cytologic Transformation in Cutaneous T-Cell Lymphoma: A Clinicopathologic Entity Associated with Poor Prognosis" Journal of Clinical Oncology 5(2):208-215, The American Society of Clinical Oncology.

Fotoohi, et al., (2004) "Disparate Mechanisms of Antifolate Resistance Provoked by Methotrexate and its Metabolite 7-Hydroxymethotrexate in Leukemia cells: Implications for Efficacy of Methotrexate Therapy" Blood 104:4194-4201 American Society of Hematology.

Fouchard et al., (1998) "Cutaneous T cell lymphomas: mycosis fungoides, Sezary syndrome and HTLV associated adult T cell leukemia (ATL) in Mali, West Africa: a clinical, pathological and immunovirological study of 14 cases and a review of the African ATL cases." Leukemia, 12:578-585.

Fry et al., (1987) "Biological and Biochemical Properties of New Anticancer Folate Antagonists" Cancer and Metastasis Reviews 5:251-270, Martinus Nijoff Publishers, Boston.

Fury et al., (2006) "A Phase I Clinical Pharmacologic Study of Pralatrexate in Combination of with Probenecid in Adults with Advance Solid Tumors" Cancer Chemother Pharmacol. 57:671-677, Springer-Vertag.

Galpin et al., (1997) "Differences in Folylpolyglutamate Synthetase and Dihydrofolate Reductase Expression in Human B-Lineage Versus T-Lineage Leukemic Lymphoblasts: Mechanisms for Lineage Differences in Methotrexate Polyglutamylation and Cytotoxicity" Molecular Pharmacology 52:155-163, The American Society for Pharmacology and Experimental Therapeutics.

Gangjee et al., (1995) "Effect of Bridge Region Variation on Antifolate and Antitumor Activity of Classical 5-Substitued 2,4-Diaminofuro [2,3-d] Pyrimidines" J. Med. Chem. 38:3798-3805, American Chemical Society.

Girardi et al., (2004) "The Pathogenesis of Mycosis Fungoides" The New England Journal of Medicine 350(19):1978-1988, Massachusetts Medical Society.

Gisselbrecht et al. (1998) "Prognostic Significance of T-Cell Phenotype in Aggressive Non-Hodgkin's Lymphomas" Blood 92(1):76-82, The American Society of Hematology.

Grenzebach et al., (2001) "Favorable Outcome for Children and Adolescents with T-cell Lymphoblastic Lymphoma with an Intensive ALL-type Therapy Without Local Radiotherapy" Ann. Hematol. 80:B73-B76, Springer-Verlag.

Hallermann et al., (2007) "Regulatory T-Cell Phenotype in Association with Large Cell Transformation of Mycosis Fungoides" European Journal of Haematology78:260-263, Blackwell Munksgaard.

Haynes, et al., (1968) "Therapy of Mycosis Fungoides" Progress in Dermatology 3:1-5, Dermatology Foundation.

Holm et al., (1980) "High and Low Affinity Binding of Folate to Proteins in Serum of Pregnant Women" Biochimica et Biophysica Acta 629:539-545, Elsevier/North-Holland Biomedical Press.

Hoovis and Chu (1973) "Enhancement of the Antiproliferative Action of 1-β-D-Arabinofuranosylcytosine by Methotrexate in Murine Leukemic Cells (L5178Y)" Cancer Research 33:521-525.

Howard and Smoller (2000) "Mycosis Fungoides: Classic Disease and Variant Presentations" 19(2):91-99, Departments of Pathology and Dermatology, Seminars in Cutaneous Medicine and Surgery.

Huennekens et al., (1994) "The Methotrexate Story: A Paradigm for Development of Cancer Chemotherapeutic Agents" Advan. Enzyme Regul. 34:397-419, Elsevier.

Kamarashev et al., (2007) "Mycosis Fungoides—Analysis of the Duration of Disease Stages in Patients Who Progress and the Tim Point of High-Grade Transformation," International Journal of Dermatology 46:930-935; The International Society of Dermatology.

Khokhar et al., (2001) "Experimental Therapeutics with a New 10-Deazaaminopterin in Human Mesothelioma: Further Improving Efficacy Through Structural Design, Pharmacologic Modulation at the Level of MRP ATPases and Combined Therapy with Platinums" Clinical Cancer Research 7:3199-3205.

Krug et al., (2000) "Phase I and Pharmacokinetic Study of 10-Propargyl-10-deazaaminopterin, a New Antifolate" Clincial Cancer Research 6:3493-3498.

Krug et al, (2003) "10-propargyl-10-deazaaminopterin: An Antifolate with Activity in Patients with Previously Treated Non-small Cell Lung Cancer" Clinical Cancer Research 9:2072-2078.

Krug et al., (2007) "Phase II Trial of Pralatrexate (10-Propargyl-10-deazaaminoptrein, PDX) in Patients with Unresectable Malignant Pleural Mesothelioma" Journal of Thoracic Oncology, 2(4):317-320.

Li et al. (2007) Clin Cancer Res 13:3413-3422 "Schedule-Dependent Cytotoxic Synergism of Pemetrexed and Erlotinib in Human Non-Small Cell Lung Cancer Cell".

Liang et al., (1992) "Intensive chemotherapy for peripheral T-cell lymphomas." Hematological Oncology, 10:155-161.

Leclerc et al., (2006) "Analysis of Folylpoly-γ-glutamate Synthetase Gene Expression in Human B-precursor ALL and T-lineage ALL Cells" BMC Cancer 6(132):1-12, BioMed Central.

Longo-Sorbello et al., (2001) "Current Understanding of Methotrexate Pharmacology and Efficacy in Acute Leukemias. Use of Newer Antifolates in Clinical Trials" Hematologica 86:121-127, Trends in Hematology.

Lundin and Österburg, (2004) "Therapy for Mycosis Fungoides" Current Treatment Options in Oncology 5:203-214, Current Science Inc.

Matsuo et al. (2001) "Association between polymorphisms of folate and methionine-metabolizing enzymes and susceptibility to malignant lymphoma" Blood, 97(10):3205-3209.

Mayne Pharma USA (2005) Methotrexate Injection, USP, Preservative Free: Package Insert, 1-26.

McDonald et al., (1974) "Cutaneous Uses of the Antiproliferative Drugs" Clinical Pharmacology and Therapeutics, 16(5):934-939.

Mercadal et al., (2008) "Intensive Chemotherapy (high-dose CHOP/ESHAP regimen) Followed by Autologous Stem-cell Transplantation in Previous Untreated Patients with Peripheral T-cell Lymphoma" Annals. Of Oncology 19:958-963, Oxford University.

Moccio et al., (1984) "Similar Specificity of Membrane Transport for Folate Analogues and Their Metabolites by Murine and Human Tumor Cells" A Clinically Directed Laboratory Study Cancer Research 44:352-357.

Molina et al., (2008) "Pralatrexate, a Dihydrofolate Reductase Inhibitor for the Potential Treatment of Several Malignancies" IDrugs 11(7):508-521, Drug Profile.

Nair et al., (1988) "Synthesis and Biological Evaluation of Poly-γ-glutamyl Metabolites of 10-Deazaaminopterin and 10-Ethyl-10-deazaaminopterin" J. Med. Chem. 181-185, American Chemical Society.

O'Connor, O. (2005) "Developing New Drugs for the Treatment of Lymphoma" European Journal of Haematology 75(Supp 66):150-158, Blackwell Munksgaard.

O'Connor et al., (2005) "Pralatrexate (10-propargyl-10-deazaaminopterin (PRX)), a Novel Antifolate, Effects Durable Complete Remissions (CR) in Patients with a Diversity of Drug Resistant T-Cell Lymphomas with Minimal Toxicity" Blood 106: Abstract 2678, American Society of Hematology.

(56) References Cited

OTHER PUBLICATIONS

O'Connor et al., (2006) "Pralatrexate: An Emerging New Agent with Activity in T-Cell Lymphomas" Current Opinion in Oncology18:591-597, Lippincott Williams & Wilkins.

O'Connor et al., (2006) "Pralatrexate (PDX) Produces Durable Complete Remissions in Patients with Chemotherapy Resistant Precursor and Peripheral T- Cell Lymphomas: Results of the MSKCC Phase I/II Experience" Blood 108: Abstract 400, American Society of Hematology.

O'Connor et al., (2007) "A Phase '2-1-2' Study of Two Different Doses and Schedules of Pralatrexate, A High Affinity Substrate for the Reduced Folate Carrier (rfc-1), in Patients with Relapsed or Refractory Lymphoma Reveals Marked Activity in T-Cell Malignancies" AACR—NCI-EORTC International Conference: Molecular Targets and Cancer Therapeutics, Oct. 22-26 2006; San Francisco, CA.

O'Connor et al., (2007) "Pralatrexate, a Novel Class of Antifol with High Affinity for the Reduced Folate Carrier Type 1, Produces Marked Complete and Durable Remissions in a Diversity of Chemotherapy Refactory Cases of T-Cell Lymphoma" British Journal of Haematology 139:425-428, Blackwell Publishing Ltd.

Olsen et al., (2007) "Revisions to the Staging and Classification of Mycosis Fungoides and Sézary Syndrome: A Proposal of the Intenational Society for Cutaneous Lymphomas (ISCL) and the Cutaneous Lymphoma Task Force of the European Organization of Research and Treatment of Cancer (EORTC)" Blood 110(6):1713-1722, The American Society of Hematology.

Paulli and Berti (2004) "Cutaneous T-Cell Lymphoma (including rare subtypes). Current concepts. II" Haematologica 89:1372-1388, Malignant Lymphomas.

Prochazkova et al., (2005) "Large Cell Transformation of Mycosis Fungoides: Tetraploidization Within Skin Tumor Large Cells" Cancer Genetics and Cytogenetics 163:1-6.

Quereux et al., (2008) "Prospective Multicenter Study of Pegylated Liposomal Doxorubicin Treatment in Patients with Advanced or Refractory Mycosis Fungoides or Sézary Syndrome" Arch. Dermatology 144(6):727-733.

Rezania et al. (2007) "The Diagnosis, Magangement, and Role of Hematopoietic Stem Cell Transplantation in Aggressive Peripheral T-Cell Neoplasms" Cancer Control 14(2):151-159.

Rizvi et al., (2006) "T-Cell Non-Hodgkin Lymphoma" Blood 107(4):1255-1264, The American Society of Hematology.

Rodriguez-Abreu et al. (2008) "Peripheral T-cell Lymphomas, unspecified (or not otherwise specified): a review." Hematol. Oncol., 26:8-20.

Rosen and Querfeld (2006) "Primary Cutaneous T-Cell Lymphomas" pp. 323-330, American Society of Hematology.

Rots et al., (1999) "Role of Folylpolyglutamate Synthetase and Folylpolyglutamate Hydrolase in Methotrexate Accumulation and Polyglutamylation in Childhood Leukemia" Blood 93:1677-1683, The American Society of Hematology.

Rots et al., (2000) "mRNA Expression Levels of Methotrexate Resistance-Related Proteins in Childhood Leukima as Determined by a Standardized Competitive Template-Based RT-PCR Method" Leukemia 14:2166-2175, Macmillian Publishers Ltd.

Rumberger et al., (1990) "Differing Specificities for 4-Aminofolate Analogues of Folylpolyglutamyl Synthetase from Tumors and Proliferative Intestinal Epithelium of the Mouse with Significance for Selective Antitumor Action" Cancer Research 50:4639-4643.

Salhany et al., (1988) "Transformation of Cutaneous T Cell Lymphoma to Large Cell Lymphoma" American Journal of Pathology 132(2):265-277, American Association of Pathologists.

Sambrook et al., (1989) "Moelcular Cloning" A Laboratory Manual, Cold Springs Harbor, Second Edition.

Samuels et al., (1985) "Similar Differential for Total Polyglutamylation and Cytotoxicity Among Various Folate Analogues in Human and Murine Tumor Cells in Vitro" Cancer Research 45:1488-1495, Presented in part at the 74$^{th}$ Annual Meeting of the American Association for Cancer Research.

Samuels et al., (1986) "Hydrolytic Cleavage of Methotrexate γ-Polyglutamates by Folylpolyglutamyl Hydrolase Derived from Various Tumors and Normal Tissues of the Mouse" Cancer Research 46:2230-2235.

Sarris et al., (2002) "Trimetrexate in Relapsed T-Cell Lymphoma With Skin Involvement" Journal of Clinical Oncology 20(12):2876-2880, The American Society of Clinical Oncology.

Savage et al., (2004) "Characterization of Peripheral T-Cell Lymphomas in a Single North American Institution by the WHO Classification" Annals of Oncology 15:1467-1475.

Savage, (2005) "Aggressive Peripheral T-Cell Lymphomas (Specified and Unspecified Types)" Hematology, pp. 267-277, American Society of Hematology.

Scott, et al., (1968) "Therapy of Mycosis Fungoides Lymphoma" Skin Cancer Panel, J.B. Lippincott Company, pp. 553-557.

Siegel et al., (2000) "Primary Cutaneous T-Cell Lymphoma: Review and Current Concepts" Journal of Clinical Oncology 18(15):2908-2925, American Society of Clinical Oncology.

Silvestri and Rivera, "Targeted Therapy for the Treatment of Advanced Non-small Cell Lung Cancer: A Review of the Epidermal Growth Factor Receptor Antagonist" Chest Journal (2005) 128:3975-3984.

Sirotnak et al., (1979) "Strereospecificity at Carbon 6 of Formyltetrahydrofolate as a Competitive Inhibitor of Transport and Cytotoxicity of Methotrexate in Vitro" Biochemical Pharmacology 28:2993-2997, Pergamon Press Ltd., Great Brittan.

Sirotnak et al., (1984) "New Folate Analogs of the 10-deaza-aminopterin Series Basis for Structural Design and Biochemical and Pharmacologic Properties" Cancer Chemotherapy Pharmacology 12:18-25, Springer-Verlag.

Sirotnak et al., (1988) "Analogs of Tetrahydrofolate Directed at Folate-dependent Purine Biosynthetic Enzymes. Characteristics of Mediated Entry and Transport-Related Resistance in L1210 Cells for 5, 10-dideazatetrahydrofolate and two 10-alkyl Derivatives" Biochemical Pharmacology 37(24):4775-4777, Pergamon Press plc., Great Brittan.

Sirotnak et al., (1993) "Markedly Improved Efficacy of Edatrexate Compared to Methotrexate in a High-Dose Regimen with Leucovorin Rescue Against Metastatic Murine Solid Tumors" Cancer Research 53:587-591.

Sirotnak et al., (1998) "A New Analogue of 10-Deazaaminopterin with Markedly Enhanced Curative Effects Against Human Tumor Xenografts in Mice" Cancer Chemotherapy Pharmacology 42:313-318, Springer-Verlag.

Sirotnak et al., (2000) "Co-Administration of Probenecid, an Inhibitor of a cMOAT/MRP-like Plasma Membrane ATPase, Greatly Enhanced the Efficacy of a New 10-Deazaaminopterin Against Human Solid Tumors in Vivo" Clinical Cancer Research, 6:3705-3712.

Skibola et al., (2004) "Polymorphisms and Haplotypes in Folate-Metabolizing Genes and Risk of Non-Hodgkin Lymphoma" Blood 104:2155-2162, www.bloodjournal.org.

Skibola et al., (2007) "Genetic Susceptibility to Lymphoma" Haematologica/The Hematology Journal 92(7):960-969.

Slater, D.N., (2005) "The New World Health Organization—European Organization for Research and Treatment of Cancer Classification for Cutaneous Lymphomas: A Practical Marriage of Two Giants" British Journal of Dermatology 153:874-880, British Association of Dermatologists.

Takimoto (1996) "New Antifolates: Pharmacology and Clinical Applications" Oncologist, 1:68-81.

Toner et al., (2006) "The Schedule-Dependent Effect of the Novel Antifolate Pralatrexate and Gemcitabine Are Superior to Methotrexate and Cytarabine in Models of Human Non-Hodgkins's Lymphoma" Clin. Cancer Res. 12(3):924-932, www.aacrjournals.org.

Ueda et al., (1986) "Inhibitory Action of 10-Deazaaminopterins and Their Polyglutamates of Human Thymidylate Synthase" Molecular Pharmacology 30:149-153, The American Society for Pharmacology and Experimental Therapeutics.

Vergier et al., (2000) "Transformation of Mycosis Fungoides: Clinicopathological and Prognostic Features of 45 Cases" 95(6):2212-2218.

(56) References Cited

OTHER PUBLICATIONS

Vrhovac et al., (2003) "A Novel Antifolate 10-propargyl-10-deazaaminopterin (PDX) Displays Synergistic Effects with Gemcitabine in Non-Hodgkin's Lymphoma Models in Vitro and in Vivo" 45th Annual Meeting of the American Society of Hematology 102(11):288b.

Vonderheid et. al., (2003) "Treatment Planning in Cutaneous T-Cell Lymphoma" Dermatologic Therapy 16:276-282.

Wang et al., (2001) "PDX, a Novel Antifolate with Potent in Vitro and in Vivo Activity in Non-Hodgkin's Lymphoma" Developmental Hematology and the Program for Molecular Pharmacology and Experimental Therapeutics, Abstract 2565.

Wang et al., (2003) "Activity of a Novel Anti-Folate (PDX, 10-Propargyl-10-Deazaaminopterin) Against Human Lymphoma is Superior to Methotrexate and Correlates with Tumor RFC-1 Gene Expression" Leukemia and Lymphoma 44(6):1027-1035.

Weidmann et al., (2004) "Diagnosis and Actual Therpay Strategies in Peripheral T-Cell Lymphomas: Summary of an International Meeting" Annals of Oncology 15:369-374.

Weinstein (1977) "Diagnosis and Treatment: Drugs Five Years Later: Methotrexate" Annals of Internal Medicine, 86:199-204.

Willemze et al., (2005) "WHO-EORTC Classification for Cutaneous Lymphomas" Blood 105(10):3768-3785, wwww.bloodjournal.org, The American Society of Hematology.

Wright et al., (2003) "Further Studies on the Interaction of Nonpolyglutamatable Aminopterin Analogs with Dihydrofolate Reductase and the Reduced Folate Carrier as Determinants of In Vitro Antitumor Activity" Biochemical Pharmacology 65:1427-1433, Elsevier.

International Search Report prepared by the U.S. Patent and Trademark Office as International Searching Authority for PCT International Patent Application No. PCT/US08/73490, dated Nov. 10, 2008, 2 pages.

Methotrexate Monograph for Professionals—Drugs.com, retrieved from http://www.drugs.com/monograph/methotrexate.html on Jun. 3, 2015, 57 pages.

JP Office Action for Application No. 2013-513352 dated May 7, 2015, 4 pages.

O'Connor et al. (2007) "Pralatrexate, a novel class of antifol with high affinity for the reduced folate carrier-type 1, produces marked complete and durable remissions in a diversity of chemotherapy refractory cases of T-cell lymphoma" British J of Haematology, v. 139:425-428.

O'Connor et al. (2009) "Phase II-I-II Study of Two Different Doses and Schedules of Pralatrexate, a High-Affinity Substrate for the Reduced Folate Carrier, in Patients With Relapsed or Refractory Lymphoma Reveals Marked Activity in T-Cell Malignancies" J. Clin Oncol 27: 4357-4364.

JP Office Action and Translation for 2013-524126 dated Jul. 6, 2015, 7 pages.

Garraway et al. (2012) "Circumventing Cancer Drug Resistance in the Era of Personalized Medicine" downloadad from cancerdiscovery.aacrjournals.or on Jul. 30, 2015, published onlinefirst Feb. 28, 2012, pp. 214-226.

Izbicka, E. et al. IDD The Institute for Drug Development A Division of the Cancer Therapy & Research Center "Differential Activity and Potential Mechanism of Action of Pralatrexate (PDX), Methotrexate (MTX), and Pemetrexed (Alimta®) In Human Cancer Models In Vivo and In Vitro". Poster session presented at the CTRC IDD in San Antonio TX, USA and Allos Therapeutics, Inc. Westminster, CO USA.

Allos, Inc. (2009) Folotyn: Highlights of Prescribing Information. Retrieved from <http://www.accessdata.fda.gov/drugsatfda_docs/label/2009/022468lbl.pdf> on Jul. 29, 2015.

Zelenetz, A. et al. (2011) "Non-Hodgkin's Lymphomas: Clinical Practice Guidelines in Oncology", JNCCN—Journal of the National Comprehensive Cancer Network vol. 9 No. 5. Retrieved from <http://www.jnccn.org/content/9/5/484.full.pdf> on Jul. 29, 2015.

Gonzalez-Angulo AM, Morales-Vasques F, Hortobagyi GN. Overview of Resistance to Systemic Therapy in Patients with Breast Cancer. In: Madame Curie Bioscience Database [Internet].

Serova et al. (2011) "Single agent and combination studies of pralatrexate and molecular correlates of sensitivity" British Journal of Cancer, v. 104:272-280.

Solheim et al. "High-dose methotrexate in the treatment of malignant mesothelioma of the pleura. A phase II study", Br. J. Cancer (1992), 65:956-960.

Hong et al "A prospective randomized trial of methotrexate versus cisplatin in the treatment of recurrent squamous cell carcinoma of the head and neck", Cancer (1983), 52(2):206-210.

Izbicka et al. "Differential activity and potential mechanism of action of pralatrexate (PDX) methotrexate, and pemetrexed (Alimta) in human cancer models in vivo and in vitro", "Molecular Cancer Therapeutics", 6:1-2.

Giovannetti et al. "Interaction between gemcitabine and topotecan in human non-small-cell lunb cancer cells: effects on cell survival, cell cycle and pharmacogenetic profile", British Journal of Cancer (2005), vol. 92:681-689.

Kano et al. "Schedule-dependent interaction between paclitaxel and 5-fluorouracil in human carcinoma cell lines in vitro", British Journal of Cancer (1996), vol. 74:704-710.

Tsai et al. "Antagonism between Gefitinib and Cisplatin in Non-small Cell Lung Cancer Cells", Journal of Thoracic Oncology, vol. 6(3): 559-568.

Canadian Examination Report for application No. 2,788,554 dated Nov. 23, 2015.

Ho et al. "A phase II study of pralatrexate with vitamin B12 and folic acid supplementation for previously treated recurrent and/or metastatic head and neck squamous cell cancer", Invest New Drugs (2014), 32(3):549-554.

Baselga, "Why the Epidermal Growth Factor Receptor? The Rationale for Cancer Therapy", The Oncologist 2002;7(suppl 4):2-8.

COMBINATION OF 10-PROPARGYL-10-DEAZAAMINOPTERIN AND ERLOTINIB FOR THE TREATMENT OF NON-SMALL CELL LUNG CANCER

RELATED APPLICATIONS

The instant application claims priority to and is a continuation in part of U.S. Ser. No. 12/779,852, filed May 13, 2010, entitled "Methods For Assessing Cancer For Increased Sensitivity To 10-Propargyl-10-Deazaminopterin By Assessing EGFR Levels," which claims priority to and is a continuation in part of U.S. Ser. No. 12/193,518, filed Aug. 18, 2008, entitled "Combination of 10-Propargyl-10-Deazaminopterin and Erlotinib for the Treatment of Non-Small Cell Lung Cancer," which claims priority to U.S. Ser. No. 60/956,525, filed Aug. 17, 2007, entitled "Combination of 10-Propargyl-10-Deazaminopterin and Erlotinib for the Treatment of Non-Small Cell Lung Cancer," and to U.S. Ser. No. 61/044,823, filed Apr. 14, 2008, entitled "Combination of 10-Propargyl-10-Deazaminopterin and Erlotinib for the Treatment of Non-Small Cell Lung Cancer," each of which is incorporated herein in their entirety by reference for all that they teach and disclose.

TECHNICAL FIELD

The present invention relates to methods to treat non-small cell lung cancer with combinations of 10-propargyl-10-deazaaminopterin and an EGFR Kinase inhibitor, including erlotinib.

BACKGROUND OF THE INVENTION

Figure 1:
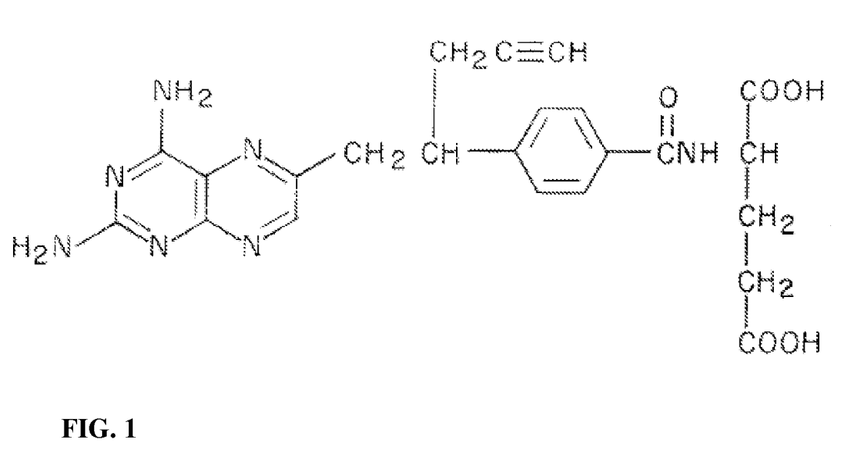
FIG. 1 shows the structure of PDX and methotrexate.

10-Propargyl-10-deazaaminopterin (variously referred to herein as "10-propargyl-10-dAM", "pralatrexate" or "PDX") is a member of a large class of compounds which have been tested and in some cases found useful in the treatment of cancer. This compound, which has the structure shown in FIG. 1, was disclosed by DeGraw et al., "Synthesis and Antitumor Activity of 10-Propargyl-10-deazaaminopterin," J. Med. Chem. 36: 2228-2231 (1993) and shown to act as an inhibitor of the enzyme dihydrofolate reductase ("DHFR") and as an inhibitor of growth in the murine L1210 cell line. In addition, some results were presented for the antitumor properties of the compound using the E0771 murine mammary tumor model.

U.S. Pat. No. 6,028,071 and PCT Publication No. WO 1998/02163, incorporated herein by reference in their entireties, disclose the surprising observation that more highly purified PDX compositions when tested in a xenograft model for their efficacy against human tumors have now been shown to be far superior to methotrexate ("MTX") and are even superior to edatrexate ("EDX"), a more recent clinical candidate. Moreover, PDX showed a surprising ability to cure tumors such that there was no evidence of tumor growth several weeks after the cessation of therapy. Thus, a highly purified composition containing PDX can be used in accordance with the invention to treat tumors, including both solid tumors and leukemias. The composition is illustrated for use in treatment of human mammary tumors and human lung cancer.

Subsequent studies with PDX have shown that it is useful on its own and in combinations with other therapeutic agents. For example, Sirotnak et al., Clinical Cancer Research Vol. 6, 3705-3712 (2000) reports that co-administration of PDX and probenecid, an inhibitor of a cMOAT/MRP-like plasma membrane ATPase greatly enhances the efficacy of PDX against human solid tumors. PDX and combinations of PDX with platinum based chemotherapeutic agents have been shown to be effective against mesothelioma. (Khokar, et al., Clin. Cancer Res. 7: 3199-3205 (2001). Co-administration with gemcitabine (Gem), for treatment of lymphoma, has been disclosed in WO/2005/117892 (incorporated by reference herein in its entirety). Combinations of PDX with taxols are disclosed to be efficacious in U.S. Pat. No. 6,323,205, also incorporated by reference in its entirety. PDX has also shown to be effective for treatment of T-cell lymphoma, see U.S. Patent Application Publication No. 2005/0267117, also incorporated by reference herein in its entirety. Other studies have shown a method for assessing sensitivity of a lymphoma to treatment with PDX by determining the amount of reduced folate carrier-1 enzyme (RFC-1) expressed by the sample, wherein a higher level of expressed RFC-1 is indicative of greater sensitivity to 10-propargyl-10-dAM, disclosed in PCT Publication No. WO 2005/117892, which is incorporated by reference herein in its entirety.

Non-small cell lung cancer ("NSCLC") is the most common of the advanced solid tumors. It is usually treated by surgery or radiation therapy. Targeted therapies utilizing drugs such as erlotinib (Tarceva®) have also been used in some patients. NSCLC refers to a subset of cancer types that account for approximately 70% of lung cancers, including squamous cell carcinoma of the lung, large cell carcinoma of the lung, and adenocarcinoma of the lung. There are more than 1.2 million new cases of lung and bronchial cancer each year worldwide, causing approximately 1.1 million deaths annually. According to the American Cancer Society, lung cancer is the most common cancer-related death in both men and women. An estimated 162,460 deaths, accounting for about 29 percent of all cancer deaths, are expected to occur in the U.S. in 2006. In Europe, it is estimated that there were approximately 381,500 new cases of lung cancer in 2004 and 936 deaths every day. Lung cancer is reported to be the single largest cause of cancer deaths in the world, responsible for 17.6 percent of all cancer deaths.

Figure 2:
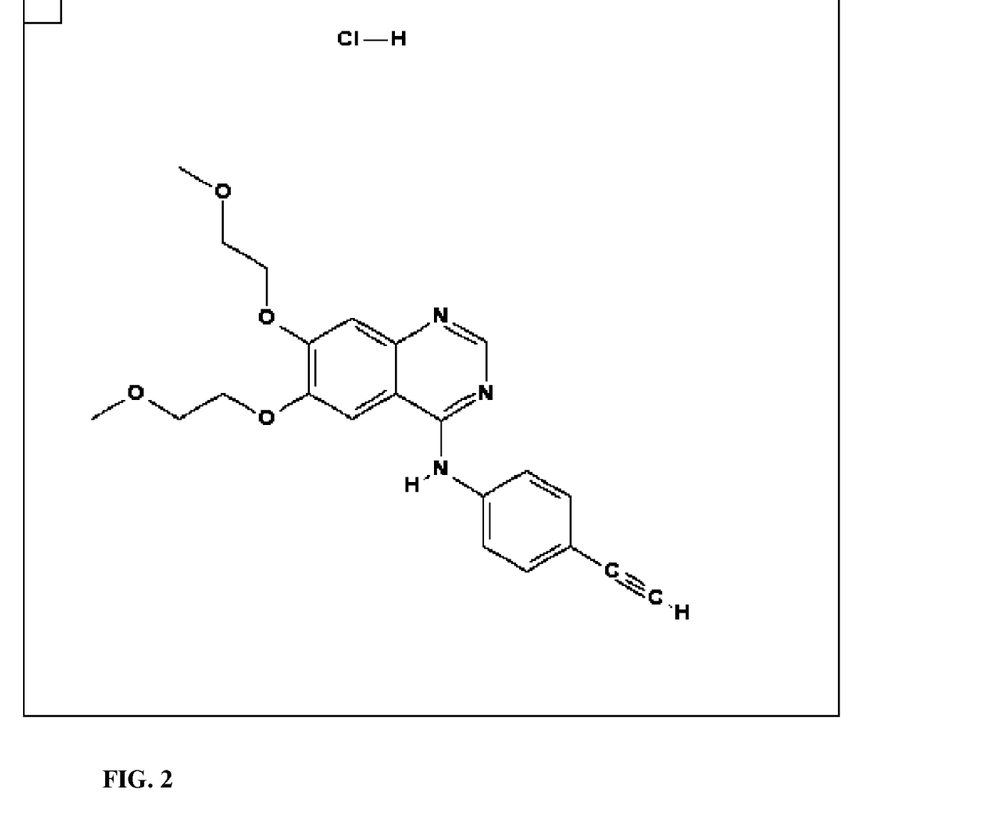
FIG. 2 shows the structure of erlotinib (Tarceva®)

Tarceva® (FIG. 2) is a small molecule human epidermal growth factor type 1/epidermal growth factor receptor (HER1/EGFR) inhibitor which demonstrated, in a Phase III clinical trial, an increased survival in advanced NSCLC patients. Tarceva® is a small molecule designed to target the human epidermal growth factor receptor (HER1) pathway, which is one of the factors critical to cell growth in non-small cell lung and pancreatic cancers. HER1, also known as EGFR, is a component of the HER signaling pathway, which plays a role in the formation and growth of non-small cell lung and pancreatic cancers. Tarceva® is designed to inhibit the tyrosine kinase activity of HER1/EGFR, thereby impeding the HER1/EGFR signaling pathway inside the cell. Tarceva® (also known as erlotinib) has the IUPAC name N-(4-ethynylphenyl)-6,7-bis(2-methoxyethoxy)quinazolin-4-amine hydrochloride[6,7-bis(2-methoxyethoxy)-4-quinazolin-4-yl]-(3-ethynylphenyl)amine (also known as OSI-774, erlotinib, or Tarceva® (erlotinib HCl); OSI Pharmaceuticals/Genentech/Roche) (U.S. Pat. No. 5,747,498; International Patent Publication No. WO 01/34574, and Moyer, J. D. et al. (1997) Cancer Res. 57:4838-4848); $C_{1-1033}$ (formerly known as PD183805; Pfizer).

A need still remains in the art for better treatments for NSCLC. These and other needs are addressed by the present invention. All references cited herein, both supra and infra, are hereby incorporated by reference herein in their entireties.

SUMMARY OF THE INVENTION

In one embodiment, the present invention includes a pharmaceutical composition comprising erlotinib and 10-propargyl-10-deazaaminopterin, in a pharmaceutically acceptable carrier. In one embodiment, erlotinib in the composition is present as a hydrochloride salt. In another embodiment, the 10-propargyl-10-deazaaminopterin is substantially free of 10-deazaaminopterin.

In another embodiment, the present invention includes a method for treatment of non-small cell lung cancer in a patient, comprising administering to said patient simultaneously or sequentially a therapeutically effective amount of a combination comprising erlotinib and 10-propargyl-10-deazaaminopterin. In one embodiment, the combination of erlotinib and 10-propargyl-10-deazaaminopterin has a synergistic anti-tumor effect. In another embodiment, the erlotinib is administered at a subtherapeutically effective amount and the 10-propargyl-10-deazaaminopterin is administered at a subtherapeutically effective amount, and the combination has a synergistic anti-tumor effect. In another embodiment, the erlotinib and 10-propargyl-10-deazaaminopterin are co-administered to the patient in the same formulation. In yet another embodiment, the erlotinib and 10-propargyl-10-deazaaminopterin are co-administered to the patient by the same route. In another embodiment, the erlotinib is administered to the patient by oral administration and/or 10-propargyl-10-deazaaminopterin is administered to the patient by oral administration.

In one embodiment, 10-propargyl-10-deazaaminopterin is administered in an amount of from about 1 to about 4 mg/kg per dose. In another embodiment, the 10-propargyl-10-deazaaminopterin is administered in a dose of about 2 mg/kg. In another embodiment, the erlotinib is administered in a dose of about 50 mg/kg.

The present invention also includes a method for the treatment of non-small cell lung cancer, comprising administering to a patient either sequentially or simultaneously a combination comprising (i) a sub-therapeutic amount of erlotinib, and (ii) a sub-therapeutic amount of 10-propargyl-10-deazaaminopterin. In one embodiment, the combination of erlotinib and 10-propargyl-10-deazaaminopterin has a synergistic anti-tumor effect. In another embodiment, the erlotinib and 10-propargyl-10-deazaaminopterin are co-administered to the patient in the same formulation. In yet another embodiment, the erlotinib and 10-propargyl-10-deazaaminopterin are co-administered to the patient by the same route. In another embodiment, the erlotinib is administered to the patient by oral administration and/or 10-propargyl-10-deazaaminopterin is administered to the patient by oral administration.

In one embodiment, 10-propargyl-10-deazaaminopterin is administered in an amount of from about 1 to about 4 mg/kg per dose. In another embodiment, the 10-propargyl-10-deazaaminopterin is administered in a dose of about 2 mg/kg. In another embodiment, the erlotinib is administered in a dose of about 50 mg/kg.

DETAILED DESCRIPTION OF THE INVENTION

The present invention relates to methods and compositions effective to treat non-small cell lung cancer. The inventor has surprisingly found that PDX, in combination with an EGFR inhibitor, including erlotinib, is effective at decreasing tumor growth in a xenograft mouse model for NSCLC at a well-tolerated dose, in a synergistic manner. Dosing with a combination of PDX and erlotinib can optionally be carried out in a sub-therapeutic dosage relative to each individual component, providing greater than additive inhibitory effects upon the growth of the tumor.

As set forth in greater detail in the examples herein, combination therapy using PDX and Tarceva® has been tested in model systems for efficacy against NSCLC. Specifically, the effect of PDX alone and in combination with Tarceva® was tested in the A549 xenograft mouse model. A549 is a human lung cancer cell line, initiated in 1972 by D. J. Giard et al. through explant culture of lung carcinomatous tissue from a 58 yr-old Caucasian male, available from the American Type Culture Collection (ATCC). Surprisingly, the study found that PDX at 2 mg/kg, IP, in combination with 50 mg/kg Tarceva®, PO, is significantly more effective at controlling A549 tumor growth, compared to control and Tarceva® alone treated groups, and also compared with the PDX alone groups. PDX alone at both doses tested (1 or 2 mg/kg), showed a trend toward controlling tumor growth compared to vehicle alone. Tarceva® is customarily used at a dose of 100 mg/kg.

The results disclosed herein show that combining 50 mg/kg Tarceva® with 2 mg/kg PDX significantly reduced the in vivo growth of A549 NSCLC cell xenografts. Of note, the administration of 2 mg/kg PDX alone also inhibited the growth of the A549 xenografts in nude mice during the study period which lasted for 35 days, which is in agreement with the in vitro activity of this compound on the growth of A549 cells. In vivo, at a well-tolerated dose and schedule, the PDX-Tarceva® combination was more effective in decreasing tumor growth than either agent alone. Collectively, these results show that PDX is effective in inhibiting the in vitro and in vivo growth of NSCLC alone and in a combination with Tarceva®, in the A549 lung tumor model.

Accordingly, in one embodiment, the present invention provides a pharmaceutical composition comprising an EGFR kinase inhibitor and PDX in a pharmaceutically acceptable carrier. In one embodiment, the EGFR kinase inhibitor is erlotinib, as discussed in more detail hereinbelow. In one embodiment of the invention, the composition comprises "highly purified" PDX. As used in the specification and claims hereof, compositions which are "highly purified" contain PDX substantially free of other folic acid derivatives, particularly 10-deazaaminopterin (10-DAM), which can interfere with the antitumor activity of PDX. A composition within the scope of the invention may include carriers or excipients for formulating PDX into a suitable dosage unit form for therapeutic use, as well as additional, non-folate therapeutic agents.

PDX can be synthesized using the method disclosed in the DeGraw paper, supra or in Example 7 of DeGraw et al., U.S. Pat. No. 5,354,751, issued Oct. 11, 1994, which is incorporated herein by reference. PDX may also be synthesized by methods presented in U.S. Pat. No. 6,028,071, especially in Example 1. Such methods are incorporated by reference herein in their entireties.

For use in the present invention, PDX is advantageously formulated as part of a pharmaceutical preparation. The specific dosage form will depend on the method of administration, but may include tablets, capsules, oral liquids, and injectable solutions for intravenous, intramuscular or intraperitoneal administration. One suitable dosing schedule involves the administration of 150 mg/m$^2$ every two weeks. Alternatively, dosing may be expressed as mg/kg body weight by any manner acceptable to one skilled in the art. One method for obtaining an equivalent dosing in mg/kg body weight involves applying the conversion factor 0.025 mg/kg, for an average human, as approximately equivalent to 1 mg/m$^2$. According to this calculation, dosing of 150 mg/m$^2$ is approximately equivalent to about 3.75 mg/kg. Lower doses may of course be indicated depending on the tolerance of an individual patient, or if more frequent administration were adopted. For example, doses on the order of 40 to 120 mg/m$^2$ of body surface area/day (about 1 to 3 mg/kg body weight per day) are appropriate. Dosages of 30 mg/m$^2$ (about 0.75 mg/kg) weekly for 3 weeks followed by a one week rest, 30 mg/m$^2$ (about 0.75 mg/kg) weekly×6 weeks followed by a one week rest, or gradually increasing doses of PDX on the weekly×6 week schedule are also suitable. Higher doses could be utilized if less frequent administration were used. Thus, in a general sense, dosages of 30 to 275 mg/m$^2$ (about 0.75 to about 6.9 mg/kg) are suitably used with various dosing schedules, for example 135 to 275 mg/m$^2$ (about 3.4 to about 6.87 mg/kg) for biweekly dosages, and 30 to 150 mg/m$^2$ (about 0.75 to about 3.75 mg/kg) for weekly dosages. The determination of suitable dosages using protocols similar to those described in U.S. Pat. No. 6,323,205, which is incorporated herein by reference, is within the skill in the art. In one embodiment, the 10-propargyl-10-deazaaminopterin is administered in an amount of from about 30 to about 275 mg/m$^2$ (about 0.75 to about 6.87 mg/kg) per dose. Methods of the present invention also include administration of 10-propargyl-10-deazaaminopterin weekly; administration of 10-propargyl-10-deazaaminopterin in a dose of about 30 mg/m$^2$ (0.75 mg/kg); administration of 10-propargyl-10-deazaaminopterin in an amount of from about 30 to about 150 mg/m$^2$ (about 0.75 to about 3.75 mg/kg) per dose; administration of 10-propargyl-10-deazaaminopterin biweekly; and/or administering 10-propargyl-10-deazaaminopterin in a dosage amount of about 135 to about 275 mg/m$^2$ (about 3.4 to about 6.9 mg/kg).

In one embodiment, 10-propargyl-10-deazaaminopterin is administered in an amount of between about 1 mg/kg and about 4 mg/kg; between about 1.25 mg/kg and about 3 mg/kg; in an amount between about 1.5 mg/kg and about 2.5 mg/kg; in an amount of about 2 mg/kg (or an equivalent amount in body surface area (BSA)).

PDX and other agents such as erlotinib may be concurrently administered or utilized in combination as part of a common treatment regimen, in which the PDX and the other agent(s) are administered at different times. For example, the other agent may be administered before, immediately afterward or after a period of time (for example 24 hours) relative to the PDX administration. Thus, for purposes of this application, the term administering refers generally to concurrent administration or to sequential administration of the drugs and in either order in a parallel treatment regimen with or without a separation in time between the drugs unless otherwise specified.

In one embodiment, 10-propargyl-10-deazaaminopterin is administered at 2 mg/kg QD for five days, or two cycles of five days each, starting at the beginning of the treatment regimen.

PDX is suitably used in combination with folic acid and vitamin B12 supplementation to reduce the side effects of the treatment. For example, patients may be treated with folic acid (1 mg/m$^2$ daily starting 1 week prior to treatment with 10-propargyl-10-dAM, or alternatively 1 mg perioral (p.o.) daily not based on BSA); and B12 (1 mg/m$^2$ monthly, or alternatively given intramuscularly (I.M.) every 8-10 weeks as 1 mg (not based on BSA), or alternatively p.o. daily 1 mg (not based on BSA)).

As used herein, the term "EGFR kinase inhibitor" also refers to any EGFR kinase inhibitor that is currently known in the art or that will be identified in the future, and includes any chemical entity that, upon administration to a patient, results in inhibition of a biological activity associated with activation of the EGF receptor in the patient, including any of the downstream biological effects otherwise resulting from the binding to EGFR of its natural ligand. Such EGFR kinase inhibitors include any agent that can block EGFR activation or any of the downstream biological effects of EGFR activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the EGFR receptor, thereby making the receptor inaccessible to its natural ligand so that its normal biological activity is prevented or reduced. Alternatively, such an inhibitor can act by modulating the dimerization of EGFR polypeptides, or interaction of EGFR polypeptide with other proteins, or enhance ubiquitination and endocytotic degradation of EGFR. EGFR kinase inhibitors include but are not limited to low molecular weight inhibitors, antibodies or antibody fragments, antisense constructs, small inhibitory RNAs (i.e. RNA interference by dsRNA; RNAi), and ribozymes. In a preferred embodiment, the EGFR kinase inhibitor is a small organic molecule or an antibody that binds specifically to the human EGFR.

More specifically, EGFR kinase inhibitors can include, for example, quinazoline EGFR kinase inhibitors, pyrido-pyrimidine EGFR kinase inhibitors, pyrimido-pyrimidine EGFR kinase inhibitors, pyrrolo-pyrimidine EGFR kinase inhibitors, pyrazolo-pyrimidine EGFR kinase inhibitors, phenylamino-pyrimidine EGFR kinase inhibitors, oxindole EGFR kinase inhibitors, indolocarbazole EGFR kinase inhibitors, phthalazine EGFR kinase inhibitors, isoflavone EGFR kinase inhibitors, quinalone EGFR kinase inhibitors, and tyrphostin EGFR kinase inhibitors, such as those described in the following patent publications, and all pharmaceutically acceptable salts and solvates of said EGFR kinase inhibitors: International Patent Publication Nos. WO 96/33980, WO 96/30347, WO 97/30034, WO 97/30044, WO 97/38994, WO 97/49688, WO 98/02434, WO 97/38983, WO 95/19774, WO 95/19970, WO 97/13771, WO 98/02437, WO 98/02438, WO 97/32881, WO 98/33798, WO 97/32880, WO 97/3288, WO 97/02266, WO 97/27199, WO 98/07726, WO 97/34895, WO 96/31510, WO 98/14449, WO 98/14450, WO 98/14451, WO 95/09847, WO 97/19065, WO 98/17662, WO 99/35146, WO 99/35132, WO 99/07701, and WO 92/20642; European Patent Application Nos. EP 520722, EP 566226, EP 787772, EP 837063, and EP 682027; U.S. Pat. Nos. 5,747,498, 5,789,427, 5,650,415, and 5,656,643; and German Patent Application No. DE 19629652. Additional non-limiting examples of low molecular weight EGFR kinase inhibitors include any of the EGFR kinase inhibitors described in Traxler, P., 1998, Exp. Opin. Ther. Patents 8(12):1599-1625.

Specific preferred examples of low molecular weight EGFR kinase inhibitors that can be used according to the present invention include [6,7-bis(2-methoxyethoxy)-4-quinazolin-4-yl]-(3-ethynylphenyl)amine (also known as OSI-774, erlotinib, or Tarceva® (erlotinib HCl); OSI Pharmaceuticals/Genentech/Roche) (U.S. Pat. No. 5,747,498; International Patent Publication No. WO 01/34574, and Moyer, J. D. et al. (1997) Cancer Res. 57:4838-4848); $C_{1-1033}$ (formerly known as PD183805; Pfizer) (Sherwood et al., 1999, Proc. Am. Assoc. Cancer Res. 40:723); PD-158780 (Pfizer); AG-1478 (University of California); CGP-59326 (Novartis); PKI-166 (Novartis); EKB-569 (Wyeth); GW-2016 (also known as GW-572016 or lapatinib ditosylate; GSK); and gefitinib (also known as ZD1839 or Iressa™; Astrazeneca) (Woodburn et al., 1997, Proc. Am. Assoc. Cancer Res. 38:633). A particularly preferred low molecular weight EGFR kinase inhibitor that can be used according to the present invention is [6,7-bis(2-methoxyethoxy)-4-quinazolin-4-yl]-(3-ethynylphenyl)amine (i.e. erlotinib), its hydrochloride salt (i.e. erlotinib HCl, Tarceva®), or other salt forms (e.g. erlotinib mesylate).

Antibody-based EGFR kinase inhibitors include any anti-EGFR antibody or antibody fragment that can partially or completely block EGFR activation by its natural ligand. Non-limiting examples of antibody-based EGFR kinase inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, Cancer Res. 59:1236-1243. Thus, the EGFR kinase inhibitor can be monoclonal antibody Mab E7.6.3 (Yang, X. D. et al. (1999) Cancer Res. 59:1236-43), or Mab C225 (ATCC Accession No. HB-8508), or an antibody or antibody fragment having the binding specificity thereof. Suitable monoclonal antibody EGFR kinase inhibitors include, but are not limited to, IMC-C225 (also known as cetuximab or Erbitux™; Imclone Systems), ABX-EGF (Abgenix), EMI 72000 (Merck KgaA, Darmstadt), RH3 (York Medical Bioscience Inc.), and MDX-447 (Medarex/Merck KgaA). The invention also encompasses a pharmaceutical composition that is comprised of an EGFR kinase inhibitor and PDX combination in combination with a pharmaceutically acceptable carrier.

The present invention, accordingly, provides a method for the treatment of non-small cell lung cancer in a patient in need thereof, comprising administering to a patient either simultaneously or sequentially a therapeutically effective amount of a combination comprising an EGFR Kinase inhibitor and 10-propargyl-10-deazaaminopterin. In one embodiment, an EGFR Kinase inhibitor and/or the 10-propargyl-10-deazaaminopterin is administered in an amount that provides for a synergistic anti-tumor effect. In another embodiment of the present invention, an EGFR Kinase inhibitor and/or the 10-propargyl-10-deazaaminopterin is administered in an amount that is subtherapeutic with respect to the individual components. In one embodiment, the EGFR Kinase inhibitor is erlotinib.

The amount of EGFR kinase inhibitor administered and the timing of EGFR kinase inhibitor administration will depend on the type (species, gender, age, weight, smoker/non-smoker, etc.) and condition of the patient being treated, the severity of the disease or condition being treated, and on the route of administration. For example, small molecule EGFR kinase inhibitors can be administered to a patient in doses ranging from 0.001 to 100 mg/kg of body weight per day or per week in single or divided doses, or by continuous infusion (see for example, International Patent Publication No. WO 01/34574). In particular, erlotinib can be administered to a patient in doses ranging from 5-200 mg per day, or 100-1600 mg per week, in single or divided doses, or by continuous infusion. Another dose is 150 mg/day.

In one embodiment, an EGFR Kinase inhibitor, including erlotinib, may be administered in either a therapeutic or subtherapeutic amount for the treatment of NSCLC. In one embodiment, an EGFR Kinase inhibitor, including erlotinib, is administered in a generally subtherapeutic amount of between about 1 mg/kg and about 95 mg/kg for the duration of the treatment regimen. The treatment regimen, in one embodiment, is 35 days. An EGFR Kinase inhibitor, including erlotinib, may also be administered in an amount of between about 25 mg/kg and about 75 mg/kg or about 50 mg/kg. Therapeutic amounts of an EGFR Kinase inhibitor, including erlotinib, may also be used, including amounts of about 100 mg/kg or greater.

Antibody-based EGFR kinase inhibitors, or antisense, RNAi or ribozyme constructs, can be administered to a patient in doses ranging from 0.1 to 100 mg/kg of body weight per day or per week in single or divided doses, or by continuous infusion. In some instances, dosage levels below the lower limit of the aforesaid range may be more than adequate, while in other cases still larger doses may be employed without causing any harmful side effect, provided that such larger doses are first divided into several small doses for administration throughout the day.

For purposes of the present invention, "co-administration of" and "co-administering" PDX with an EGFR kinase inhibitor (both components referred to hereinafter as the "two active agents") refer to any administration of the two active agents, either separately or together, where the two active agents are administered as part of an appropriate dose regimen designed to obtain the benefit of the combination therapy. Thus, the two active agents can be administered either as part of the same pharmaceutical composition or in separate pharmaceutical compositions. PDX can be administered prior to, at the same time as, or subsequent to administration of the EGFR kinase inhibitor, or in some combination thereof. Where the EGFR kinase inhibitor is administered to the patient at repeated intervals, e.g., during a standard course of treatment, PDX can be administered prior to, at the same time as, or subsequent to, each administration of the EGFR kinase inhibitor, or some combination thereof, or at different intervals in relation to the EGFR kinase inhibitor treatment, or in a single dose prior to, at any time during, or subsequent to the course of treatment with the EGFR kinase inhibitor.

The EGFR kinase inhibitor and/or PDX will typically be administered to the patient in a dose regimen that provides for the most effective treatment of the cancer (from both efficacy and safety perspectives) for which the patient is being treated, as known in the art, and as disclosed, e.g. in International Patent Publication No. WO 01/34574. In conducting the treatment method of the present invention, the EGFR kinase inhibitor and/or PDX can be administered in any effective manner known in the art, such as by oral, topical, intravenous, intra-peritoneal, intramuscular, intra-articular, subcutaneous, intranasal, intra-ocular, vaginal, rectal, or intradermal routes, depending upon the type of cancer being treated, the type of EGFR kinase inhibitor being used (e.g., small molecule, antibody, RNAi or antisense construct), and the medical judgement of the prescribing physician as based, e.g., on the results of published clinical studies.

The EGFR kinase inhibitors and PDX can be administered either separately or together by the same or different routes, and in a wide variety of different dosage forms. For example, the EGFR kinase inhibitor is preferably administered orally or parenterally, and PDX is preferably administered orally or parenterally. In one embodiment, the EGFR kinase inhibitor is administered orally. Where the EGFR kinase inhibitor is erlotinib HCl (Tarceva®), oral administration is preferable. In one embodiment, PDX is administered parenterally, and may be administered via the intravenous route.

The EGFR kinase inhibitor can be administered with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Administration of such dosage forms can be carried out in single or multiple doses. Carriers include solid diluents or fillers, sterile aqueous media and various non-toxic organic solvents, etc. Oral pharmaceutical compositions can be suitably sweetened and/or flavored.

The EGFR kinase inhibitor and PDX can be combined together with various pharmaceutically acceptable inert carriers in the form of sprays, creams, salves, suppositories, jellies, gels, pastes, lotions, ointments, and the like. Administration of such dosage forms can be carried out in single or multiple doses. Carriers include solid diluents or fillers, sterile aqueous media, and various non-toxic organic solvents, etc.

Methods of preparing pharmaceutical compositions comprising an EGFR kinase inhibitor are known in the art, and are described, e.g. in International Patent Publication No. WO 01/34574. Methods of preparing pharmaceutical compositions comprising PDX are also well known in the art and taught herein. In view of the teaching of the present invention, methods of preparing pharmaceutical compositions comprising both an EGFR kinase inhibitor and PDX will be apparent from the above-cited publications and from other known references, such as Remington's Pharmaceutical Sciences, Mack Publishing Company, Easton, Pa., 18$^{th}$ edition (1990).

For oral administration of EGFR kinase inhibitors, tablets containing one or both of the active agents are combined with any of various excipients such as, for example, microcrystalline cellulose, sodium citrate, calcium carbonate, dicalcium phosphate and glycine, along with various disintegrants such as starch (and preferably corn, potato or tapioca starch), alginic acid and certain complex silicates, together with granulation binders like polyvinyl pyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the EGFR kinase inhibitor may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration of either or both of the active agents, solutions in either sesame or peanut oil or in aqueous propylene glycol may be employed, as well as sterile aqueous solutions comprising the active agent or a corresponding water-soluble salt thereof. Such sterile aqueous solutions are preferably suitably buffered, and are also preferably rendered isotonic, e.g., with sufficient saline or glucose. These particular aqueous solutions are especially suitable for intravenous, intramuscular, subcutaneous and intraperitoneal injection purposes. The oily solutions are suitable for intra-articular, intramuscular and subcutaneous injection purposes. The preparation of all these solutions under sterile conditions is readily accomplished by standard pharmaceutical techniques well known to those skilled in the art. Any parenteral formulation selected for administration of proteinaceous EGFR kinase inhibitors should be selected so as to avoid denaturation and loss of biological activity of the inhibitor.

Additionally, it is possible to topically administer either or both of the active agents, by way of, for example, creams, lotions, jellies, gels, pastes, ointments, salves and the like, in accordance with standard pharmaceutical practice. For example, a topical formulation comprising either an EGFR kinase inhibitor or PDX in about 0.1% (w/v) to about 5% (w/v) concentration can be prepared.

For veterinary purposes, the active agents can be administered separately or together to animals using any of the forms and by any of the routes described above. In a preferred embodiment, the EGFR kinase inhibitor is administered in the form of a capsule, bolus, tablet, liquid drench, by injection or as an implant. As an alternative, the EGFR kinase inhibitor can be administered with the animal feedstuff, and for this purpose a concentrated feed additive or premix may be prepared for a normal animal feed. The PDX is preferably administered in the form of liquid drench, by injection or as an implant. Such formulations are prepared in a conventional manner in accordance with standard veterinary practice.

The present invention further provides a kit comprising a single container comprising both an EGFR kinase inhibitor and PDX. The present invention further provides a kit comprising a first container comprising an EGFR kinase inhibitor and a second container comprising PDX. In a preferred embodiment, the kit containers may further include a pharmaceutically acceptable carrier. The kit may further include a sterile diluent, which is preferably stored in a separate additional container. The kit may further include a package insert comprising printed instructions directing the use of the combined treatment as a method for treating cancer.

Preferably the composition is comprised of a pharmaceutically acceptable carrier and a non-toxic therapeutically effective amount of an EGFR kinase inhibitor compound and PDX (including pharmaceutically acceptable salts of each component thereof). Moreover, within this preferred embodiment, the invention encompasses a pharmaceutical composition for the treatment of disease, the use of which results in the inhibition of growth of neoplastic cells, benign or malignant tumors, or metastases, comprising a pharmaceutically acceptable carrier and a non-toxic therapeutically effective amount of an EGFR kinase inhibitor compound and PDX (including pharmaceutically acceptable salts of each component thereof).

The term "pharmaceutically acceptable salts" refers to salts prepared from pharmaceutically acceptable non-toxic bases or acids. When a compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (cupric and cuprous), ferric, ferrous, lithium, magnesium, manganese (manganic and manganous), potassium, sodium, zinc and the like salts. Particularly preferred are the ammonium, calcium, magnesium, potassium and sodium slats. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylameine, trimethylamine, tripropylamine, tromethamine and the like.

When a compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The pharmaceutical compositions of the present invention comprise an EGFR kinase inhibitor compound and PDX (including pharmaceutically acceptable salts of each component thereof) as active ingredient, a pharmaceutically acceptable carrier and optionally other therapeutic ingredients or adjuvants. Other therapeutic agents may include those cytotoxic, chemotherapeutic or anti-cancer agents, or agents which enhance the effects of such agents, as listed above. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by an EGFR kinase inhibitor compound and PDX combination (including pharmaceutically acceptable salts of each component thereof) of this invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, an EGFR kinase inhibitor compound and PDX combination (including pharmaceutically acceptable salts of each component thereof) may also be administered by controlled release means and/or delivery devices. The combination compositions may be prepared by any of the methods of pharmacy. In general, such methods include a step of bringing into association the active ingredients with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

In one embodiment of this invention, a pharmaceutical composition can comprise an EGFR kinase inhibitor compound and PDX in combination with an anticancer agent, wherein said anti-cancer agent is a member selected from the group consisting of alkylating drugs, antimetabolites, microtubule inhibitors, podophyllotoxins, antibiotics, nitrosoureas, hormone therapies, kinase inhibitors, activators of tumor cell apoptosis, and antiangiogenic agents.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing an EGFR kinase inhibitor compound and PDX combination (including pharmaceutically acceptable salts of each component thereof) of this invention, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing an EGFR kinase inhibitor compound and PDX combination (including pharmaceutically acceptable salts of each component thereof) may also be prepared in powder or liquid concentrate form.

Dosage levels for the compounds of the combination of this invention will be approximately as described herein, or as described in the art for these compounds. It is understood, however, that the specific dose level for any particular patient will depend upon a variety of factors including the age, body weight, general health, sex, diet, time of administration, route of administration, rate of excretion, drug combination and the severity of the particular disease undergoing therapy.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

The following examples are provided for illustrative purposes only and are not intended to limit the scope of the invention.

Example 1

This example describes testing of 10-propargyl-10-dAM and Tarceva® for cytotoxicity against human non-small cell lung cancer cell lines.

The objective of this study was to evaluate the effect of PDX alone and in combination with Tarceva® in the A549 non-small cell lung cancer xenograft mouse model. This study consisted of two parts. In the first part, the maximum tolerated dose (MTD) for PDX and Tarceva® alone and in combination was evaluated, with emphasis on the MTD of the combination. In the second part of the study, the effect of PDX alone and in combination with Tarceva® was evaluated in the A549 xenograft mouse model. Based on the MTD evaluation, nude mice tolerated 2 mg/kg dose of PDX (two cycles—QDx5) alone and in combination with 50 mg/kg of Tarceva® (QDx30). Results showed that PDX not only in combination with Tarceva® but also alone was effective in controlling A549 tumor growth.

Materials and Methods

Test System:
  Species/Strain: Athymic nu/nu (HSD:ATHYMIC NUDE-FOXN1$^{NU}$) mice
  Physiological state: Immunodeficient mice
  Age/weight range at start of study: 4-6 week/15-18 gm
  Sex: Female
  Animal supplier: Harlan
  Number of animals/group: MTD evaluation—5 animals/group
    Xenograft study—10 animals/group
  Identification: Ear punch
  Randomization: Mean tumor volume in all groups should be within 15% of the mean tumor volume in Group 1 (control group)
  Replacement: Animals will not be replaced during the course of the study Animal Housing and Environment:
  Housing: Micro-isolator cages, 5 animals/cage
  Acclimation: 5 days
  Environmental conditions: Maintain under pathogen free environment
  Food: Irradiated certified standard fresh rodent chow
  Water: ad-libitum sterile water Test Articles:

| NAME | CODE or CAS | FORMULATION/ GENERAL INFORMATION | STORAGE CONDITIONS |
|---|---|---|---|
| Test Articles: | | | |
| PDX | | PBS | 4° C. |
| Control Article: | | | |
| Tarceva ® | NDC# 50242-0063-01 | 0.5 CMC | 4° C. |

Description of the Cell Line Used for Xenotransplant

| Tumor Type | Cell Line (Name) | Histological Origin (Condition) | Growth media | Source |
|---|---|---|---|---|
| Non-small cell lung carcinoma | A549 | Carcinoma | Ham's F12K medium with 2 mM L-glutamine 1.5 g/L sodium bi-carbonate, supplemented with 10% fetal bovine serum | ATCC |

Methods:
Cell Lines and Cell Culture:
  The human non small lung carcinoma cell line A549 was purchased from the American Type Culture Collection (ATCC, Manassas, Va.). The cell line was cultured in Ham's F 12K medium with 2 mM L-glutamine 1.5 g/L sodium bicarbonate, supplemented with 10% fetal bovine serum and was maintained at 37° C. in a humidified atmosphere at 5% $CO_2$ and 95% air.

Drug Preparations:

PDX was prepared as described in U.S. Pat. No. 6,028,071 at a concentration of 20 mg/ml (PDX-008, lot #13110606). Dosing concentrations for 1 mg/kg and 2 mg/kg were prepared in PBS for IP dosing. Tarceva® was purchased from OSI Pharmaceuticals, Inc. (Melville, N.Y.) which is distributed by Genentech, Inc (CA). Tarceva® tablets were ground into powder, suspended in 0.5% Carboxymethyl cellulose (CMC) and dosed at 50 mg/kg by oral gavages.

Animal Studies:

Female athymic nu/nu mice, weighing approximately 18 g at 6-8 weeks of age, were obtained from Harlan Sprague Dawley, Inc (Indianapolis, Ind.). All mice were maintained in a laminar airflow cabinet under specific pathogen-free conditions. All facilities were approved by the Association of Assessment and Accreditation of Laboratory Animal Care (AALAC), and all animal experiments were conducted under the institutional guidelines established by the IACUC.

Evaluation of Maximum Tolerated Dose in Non-Tumor Bearing Nude Mice:

To evaluate the doses to be tested in the xenograft mouse model, non-tumor bearing female athymice nu/nu mice were treated with 2 mg/kg of PDX alone and in combination with 50 mg/kg of Tarceva® as described in Table 1. Animals were monitored daily for routine health observation. Body weight of the animals was recorded daily during the treatment phase and thereafter twice weekly for 14 days after the last treatment).

TABLE 1

Evaluation of maximum tolerated dose (MTD in non-tumor bearing nude mice.

| Group Number | Number Of Animals Per Group | Description | Comments |
|---|---|---|---|
| 1 | 5 | PBS and 0.5% CMC | Route: IP/PO; PBC (QDx5 for two cycles) plus 0.5% CMC (QDx21) |
| 2 | 5 | PDX (2 mg/kg) | Route: IP; QD x 5 for two cycles |
| 3 | 5 | Tarceva (50 mg/kg) alone | Route: PO; QD |
| 4 | 5 | PDX (2 mg/kg) plus Tarceva (50 mg/kg) | Route: IP/PO; PDX (QDx5 for two cycles) plus Tarceva (QDx21) |

Establishment of Tumor Growth:

Xenotransplant of A549 was established by subcutaneous inoculation of $5 \times 10^6$ cells on the right flank using a 21G needle in 6-8 week female athymic nude mice. A total of 75 animals were injected with A549 xenotransplant. Tumor volume was monitored twice weekly, once the established tumor reached 75-150 mm³ (individual tumor range between 70 to 200 mm³) the mice were randomized to the different groups as described in Table 2.

Tumor Measurements:

Tumor volume and body weights were measured twice weekly up to 58 days following A549 inoculation. Tumor volume was calculated using the following formula: Tumor volume=$(A^2 \times B/2)$ where A is the smallest diameter and B is the largest diameter.

Drug Treatment:

The treatment was initiated on the day of randomization according to the schedule described in Table 2. PDX was administered via IP injection and Tarceva® by oral gavage. PBS and 0.5% CMC were administrated to Group 1 as control vehicles by IP and PO routes, respectively.

TABLE 2

Dosing regimen of PDX alone and in combination with Tarceva ® in A549 xenograft mouse model

| Group Number | Number Of Animals Per Group | Description | Dosing/Schedule |
|---|---|---|---|
| 1 | 10 | Vehicle | PO (0.1 ml) OD |
| 2 | 10 | PDX (1 mg/kg) | IP (0.1 ml) QDx5 for two cycles |
| 3 | 10 | PDX (2 mg/kg) | IP (0.1 ml) QDx5 for two cycles |
| 4 | 10 | Tarceva (50 mg/kg) | PO (0.1 ml) OD |
| 5 | 10 | Tarceva/PDX 50 mg/kg/ 1 mg/kg | PO/IP (0.1 ml/0.1 ml) OD/QDx5 for two cycles |
| 6 | 10 | Tarceva/PDX 50 mg/kg/ 2 mg/kg | PO/IP (0.1 ml/0.1 ml) OD/QDx5 for two cycles |

Statistical Methods:

Statistical analysis was performed using Graphpad Prism software. Comparison between control group and treatment groups was performed using 2 way ANOVA analysis.

Results

Evaluation of IC50 in A549 Cells

An in vitro study in A549 cells was performed to compare the growth inhibition activity of PDX to that of cisplatin, paclitaxel, and docetaxel. The results are shown in Table 3.

TABLE 3

| Compound | IC50 (nM) |
|---|---|
| Pralatrexate | 65.1 |
| Cisplatin | 22.4 |
| Paclitaxel | 108.7 |
| Docetaxel | 23.6 |

Figure 3:
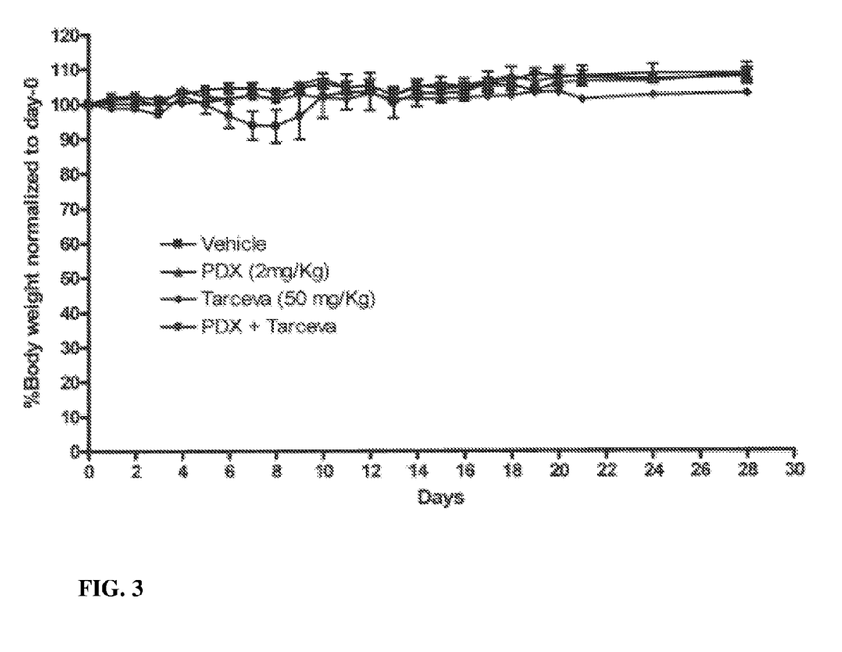
FIG. 3 shows body weight evaluation of maximum tolerated dose in non-tumor bearing nude mice.
Figure 4:
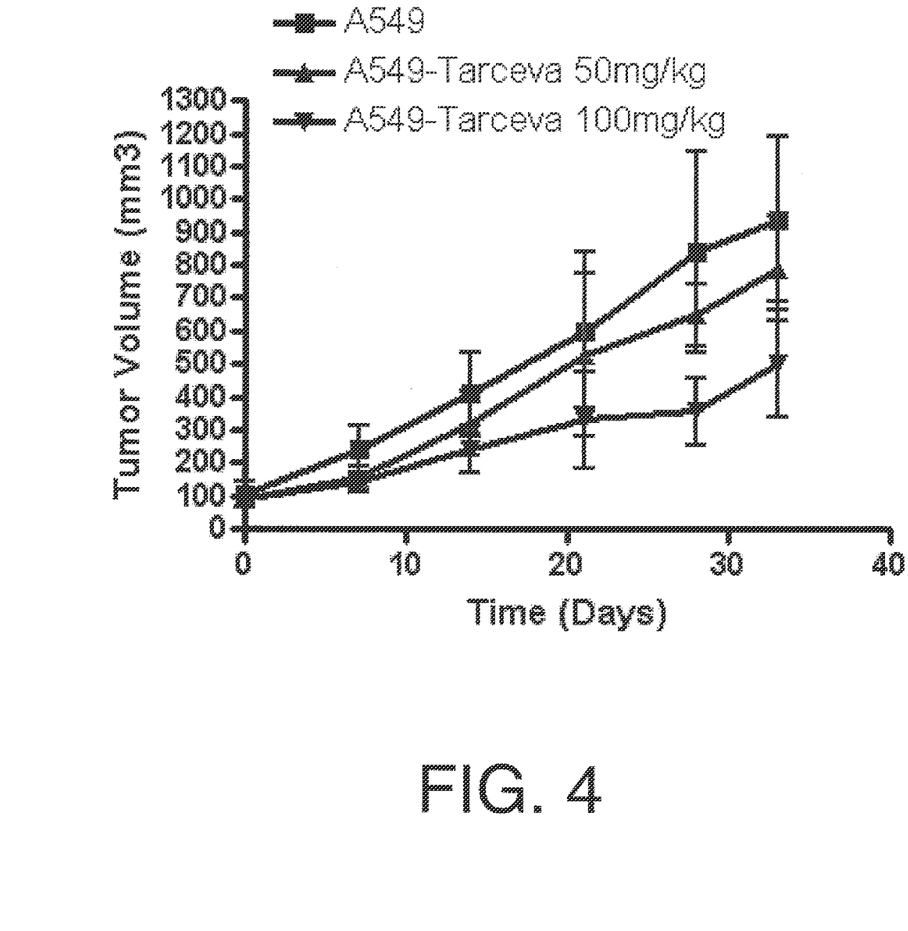
FIG. 4 shows effect of Tarceva® on tumor volume in A549 xenograft mouse model.

Evaluation of Maximum Tolerated Dose in Non-Tumor Bearing Nude Mice:

In the MTD study, non-tumor bearing mice were exposed to PDX at 2 mg/kg of PDX (QDx5 for 2 cycles) alone and in combination with 50 mg/kg of Tarceva® (50 mg/kg (QDx21). FIG. 3 represents the day-0 normalized body weights over the study period. Two of the five animals receiving PDX plus Tarceva® showed significant decrease in body weight over the period of 3 days at days 7, 8, and 9. These animals recovered the loss in body weight after day 9 of treatment. The maximum tolerated dose of the combination was determined as PDX 2 mg/kg+Tarceva® 50 mg/kg. Hence, a single dose of PDX or Tarceva® was well tolerated and the combination was acceptably tolerated in this study. For comparison, FIG. 4 presents a comparison of the relative tumor volume in mice with A549 xenografts exposed to Tarceva® at 50 and 100 mg/kg.

Figure 5:
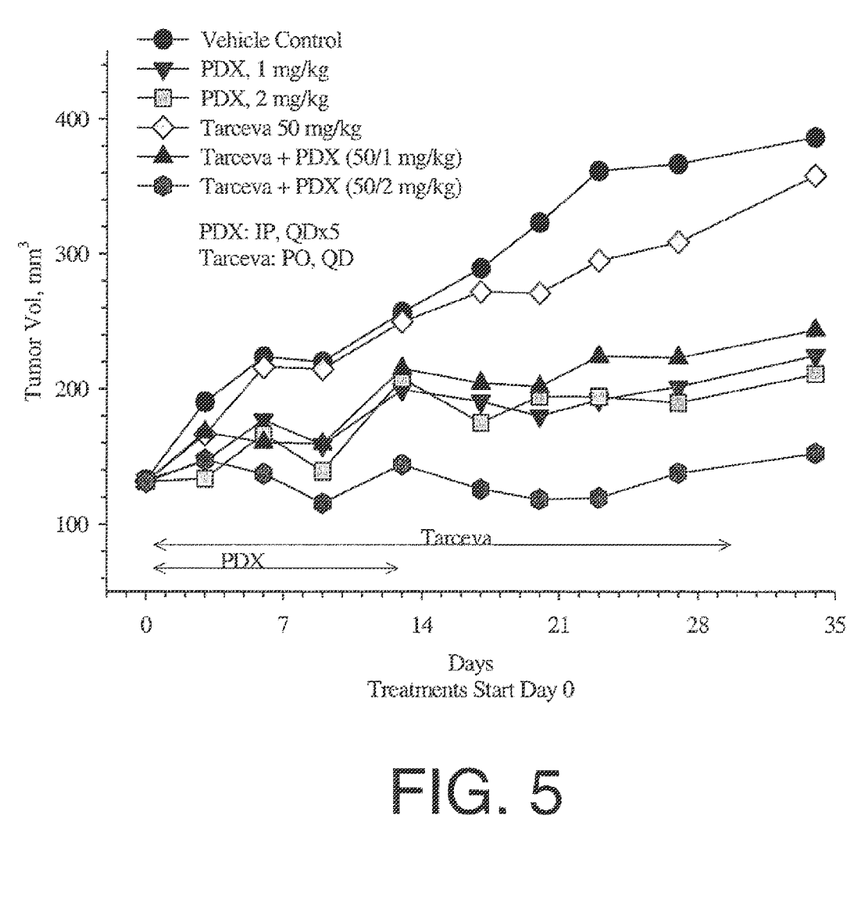
FIG. 5 shows the effect of PDX alone and in combination with Tarceva® on tumor volume in A549 xenograft mouse model.

Evaluation of PDX Alone and in Combination with Tarceva® in A549 Xenograft Tumor Model:

Seventy five nude female mice were inoculated subcutaneously in the right flank with $5 \times 10^6$ A549 cells to establish the xenotransplant. Tumor volume and body weights were monitored twice a week. Once the established tumor reached 75-150 mm$^3$ (individual tumor range between 70 to 200 mm$^3$) the mice were randomized to a treatment group as described in Table 2 above. The mean tumor volume in each of the treatment groups was within less than 1% that of mean tumor volume in the vehicle control group. Treatment was initiated on the day of randomization according to the schedule described in Table 2 above. One mouse each from group 5 and 6 was eliminated from the analysis due to ulceration of tumor. FIG. 5 represents the effect of PDX alone and in combination with Tarceva® on tumor growth over a period of 35 days following start of therapy. PDX was administered by IP injection and Tarceva® by oral gavage. Phosphate buffered saline and 0.5% carboxymethylcellulose were administered to Group 1 as control vehicles. PDX alone and in combination with Tarceva® showed better control of tumor growth, compared to the vehicle group, than the Tarceva® alone treated group. Interestingly, PDX at a dose of 2 mg/kg in combination with Tarceva® at 50 mg/kg showed significant tumor growth inhibition over the time period studied, compared to vehicle, PDX or Tarceva® alone groups. Also both the PDX alone groups (1 mg/kg and 2 mg/kg) and PDX (1 mg/kg) in combination with Tarceva® (50 mg/kg) showed a trend in reducing tumor growth, whereas Tarceva® alone at 50 mg/kg did not control tumor growth. FIG. 5 summarizes the comparison of tumor volume over time. Mean±SD tumor volume at the end of study (at 35$^{th}$ day following start of therapy) was 386±244 mm$^3$, 224±128 mm$^3$, 210±109 mm$^3$, 358±282 mm$^3$, 243±122 mm$^3$ and 152±85 mm$^3$ in control, PDX (1 mg/kg), PDX (2 mg/kg), Tarceva® (50 mg/kg), PDX (1 mg/kg)+Tarceva® (50 mg/kg) and PDX (2 mg/kg)+Tarceva® (50 mg/kg), respectively.

Table 4 shows the effect of PDX/Tarceva® in A549 mouse model compared between control and treatment groups over the study period performed by 2-way ANOVA analysis using PRISM software.

mg/kg was significantly more effective in controlling A549 tumor growth, compared to control and Tarceva®-alone treated groups. PDX at 2 mg/kg in combination with Tarceva® was more effective in controlling tumor growth than either agent alone. PDX was shown to be effective at controlling tumor growth in this NSCLC xenograft model and may be a promising agent in the treatment of NSCLC.

Example 2

This Example describes the differential activity and potential mechanism of action of pralatrexate (PDX) methotrexate, and pemetrexed (Alimta) in human cancer models in vivo and in vitro.

Methods: This pilot study investigated activity and potential mechanism of action of PDX that differentiates it from other antifolates. We compared in vivo activity of PDX and MTX (both at 1 mg/kg and 2 mg/kg), Alimta (150 mg/kg) against MV522 and H460 non-small cell lung carcinoma human tumor xenografts. Endpoints included mean tumor growth inhibition or regression. We further evaluated activity and/or expression of folate-dependent enzymes: DHFR, thymidylate synthase (TS), and folylpolyglutamate synthase (FPGS) using kinetic assays and immunostaining in tumors harvested at the end of the study from animals treated with the antifolates or vehicle controls. In vitro studies included evaluation of reduced folate carrier (RFC) expression by quantitative RT-PCR in MV522, and H460, xenograft models. We also compared the short-term uptake (assessment of RFC-1 transporter) and on FPGS activity (polyglutamylation) of radiolabeled PDX, MTX (both at 5 μM) and Alimta (20 μM) in H460 cells in vitro. Inhibition of DHFR by the three antifolates was quantified in a cell-free assay against human recombinant DHFR.

Results and conclusions: In vivo, PDX dose-dependently inhibited tumor growth in H460 and MV522 xenografts with greater activity seen in the more rapidly growing H460

TABLE 4

| | Control | | PDX (1 mg/kg) | | PDX (2 mg/kg) | | Tarceva (50 mg/kg) | | PDX (1 mg/kg) + Tarceva (50 mg/kg) | | PDX (2 mg/kg) + Tarceva (50 mg/kg) | |
|---|---|---|---|---|---|---|---|---|---|---|---|---|
| Days | Avg ± SD | P value* | Avg ± SD | P value | Avg ± SD | P value | Avg ± SD | P value | Avg ± SD | P value | Avg ± SD | P value |
| 0 | 132 ± 54. | — | 132 ± 52. | P > 0.05 | 131 ± 49. | P > 0.05 | 131 ± 47. | P > 0.05 | 131 ± 45. | P > 0.05 | 131 ± 42. | P > 0.05 |
| 3 | 190 ± 84. | — | 148 ± 67. | P > 0.05 | 133 ± 60. | P > 0.05 | 166 ± 80. | P > 0.05 | 167 ± 74. | P > 0.05 | 147 ± 73. | P > 0.05 |
| 7 | 223 ± 81. | — | 176 ± 87. | P > 0.05 | 166 ± 75. | P > 0.05 | 216 ± 121 | P > 0.05 | 160 ± 70. | P > 0.05 | 137 ± 56. | P > 0.05 |
| 10 | 219 ± 132 | — | 158 ± 93. | P > 0.05 | 139 ± 70. | P > 0.05 | 214 ± 140 | P > 0.05 | 159 ± 76. | P > 0.05 | 104 ± 66. | P > 0.05 |
| 14 | 256 ± 130 | — | 199 ± 79. | P > 0.05 | 207 ± 100 | P > 0.05 | 249 ± 130 | P > 0.05 | 214 ± 71. | P > 0.05 | 129 ± 67. | P > 0.05 |
| 17 | 289 ± 155 | — | 190 ± 78. | P > 0.05 | 174 ± 104 | P > 0.05 | 271 ± 206 | P > 0.05 | 204 ± 96. | P > 0.05 | 113 ± 61. | P < 0.05 |
| 21 | 323 ± 226 | — | 179 ± 112 | P > 0.05 | 194 ± 114 | P > 0.05 | 270 ± 210 | P > 0.05 | 201 ± 102 | P > 0.05 | 118 ± 40. | P < 0.01 |
| 24 | 361 ± 213 | — | 191 ± 105 | P < 0.05 | 194 ± 101 | P > 0.05 | 294 ± 261 | P > 0.05 | 224 ± 115 | P > 0.05 | 119 ± 83. | P < 0.001 |
| 28 | 366 ± 230 | — | 201 ± 114 | P > 0.05 | 189 ± 106 | P < 0.05 | 308 ± 280 | P > 0.05 | 223 ± 117 | P > 0.05 | 137 ± 80. | P < 0.01 |
| 35 | 386 ± 244 | — | 224 ± 128 | P > 0.05 | 210 ± 109 | P < 0.05 | 357 ± 282 | P > 0.05 | 243 ± 122 | P > 0.05 | 152 ± 85. | P < 0.01 |

*Comparison between control and treatment group over a study period was performed by 2-way ANOVA analysis using prism software.

In summary, this Example shows the effect of pralatrexate (PDX) alone and in combination with Tarceva® on tumor growth inhibition in the A549 non-small cell lung cancer (NSCLC) cells and xenograft mouse model (female athymic nu/nu mice). An initial dose range finding study identified the maximum tolerated doses of PDX and Tarceva® alone and in combination in mice. In the tumor growth study, the effect of Tarceva® alone (50 mg/kg, PO, QDx30), PDX alone (1 mg/kg and 2 mg/kg, IP, two cycles—QDx5) or the combination of Tarceva® (50) and PDX (1 and 2) on subcutaneous A549 NSCLC growth was monitored for 35 days. PDX at 2 mg/kg in combination with Tarceva® at 50 model. The activity of MTX and Alimta was also model-dependent, with PDX being more active than MTX or Alimta in each tumor xenograft model. RFC expression was below the assay detection limit in MV522 and H460 cells. PDX, Alimta and MTX exerted qualitative differences on TS enzymatic activity and protein expression, and DHFR protein content in H460 and MV522 tumor xenografts. Unlike Alimta and MTX, PDX down-regulated most of these endpoints.

Apparent Ki values for DHFR inhibition in a cell-free assay were, respectively, 45 nM, 26 nM, and >200 nM for PDX, MTX, and Alimta, respectively. The total uptake of radiolabeled drugs measured at 15 and 60 minutes was similar at both times (MTX), decreased later (Alimta), or increased over time (PDX). A significantly smaller fraction of radiolabeled MTX entered the cells in comparison with PDX or Alimta. Radiolabeled species (conceivably polyglutamylated PDX) with a bell-shaped distribution of different Rf values than the drug alone appeared in a time-dependent manner in lysates from PDX-treated cells with much lesser polyglutamylation seen in MTX or Alimta-treated cells, suggesting greater polyglutamylation of PDX than either MTX or Alimta. The results from this pilot study suggest that PDX has a different activity profile relative to MTX and Alimta. Some of the observed differences include enhanced uptake of PDX into the cell and subsequent greater intracellular polyglutamylation that translate into greater tumor growth inhibition by PDX than either MTX or Alimta in NSCLC xenograft models in vivo.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for treatment of non-small cell lung cancer in a patient, comprising administering to said patient simultaneously or sequentially a therapeutically effective amount of a combination comprising an EGFR inhibitor and 10-propargyl-10-deazaaminopterin, wherein the combination of the EGFR inhibitor and 10-propargyl-10-deazaaminopterin has a synergistic anti-tumor effect, wherein the EGFR inhibitor is erlotinib.

2. The method of claim 1, wherein the erlotinib is administered in a dose of about 50 mg/kg.

3. The method of claim 1, wherein the erlotinib is administered to the patient by oral administration.

* * * * *